(12) United States Patent
Say et al.

(10) Patent No.: US 6,485,521 B1
(45) Date of Patent: Nov. 26, 2002

(54) ORTHOPEDIC IMPLANT HAVING A POROUS SURFACE AND METHOD OF MAKING SAME

(76) Inventors: Wen-Ching Say, 2F, 3, Lane 34, Ta-Chih Street, Taipei (TW); Chih-I Lin, 14292 Spring Vista La., Chino Hills, CA (US) 91709; Shengfu Lin, 3F, 7, Lane 110, Chien-Kang Street, Taipei (TW)

( * ) Notice: Subject to any disclaimer, the term of this patent is extended or adjusted under 35 U.S.C. 154(b) by 146 days.

(21) Appl. No.: 09/593,370

(22) Filed: Jun. 14, 2000

(30) Foreign Application Priority Data

Dec. 8, 1999 (TW) .......................................... 88121518 A

(51) Int. Cl.⁷ .................................................. A61F 2/02
(52) U.S. Cl. ...................................... 623/23.55; 606/76
(58) Field of Search .......................... 623/11.11, 16.11, 623/20.16, 20.17, 22.23, 22.32, 23.28, 23.29, 23.3, 23.36, 23.5, 23.53, 23.54, 23.55, 23.72, 23.74; 606/60, 70, 72, 76

(56) References Cited

U.S. PATENT DOCUMENTS 5,366,508 A * 11/1994 Brekke ........................ 424/422
5,855,608 A * 1/1999 Brekke et al. ............... 424/487
6,103,255 A * 8/2000 Levene et al. ............... 424/426

* cited by examiner

Primary Examiner—David J. Isabella
(74) Attorney, Agent, or Firm—Bacon & Thomas

(57) ABSTRACT

An orthopedic implant has a porous surface with a plurality of pores, some of which are provided with a pores-within-a-pore structure. The pores-within-a-pore structure has a pore opening ranging in size between 10 and 800 microns. The present invention also discloses a process for making an orthopedic implant which is provided in the surface thereof with a pores-within-a-pore porous structure.

10 Claims, 14 Drawing Sheets

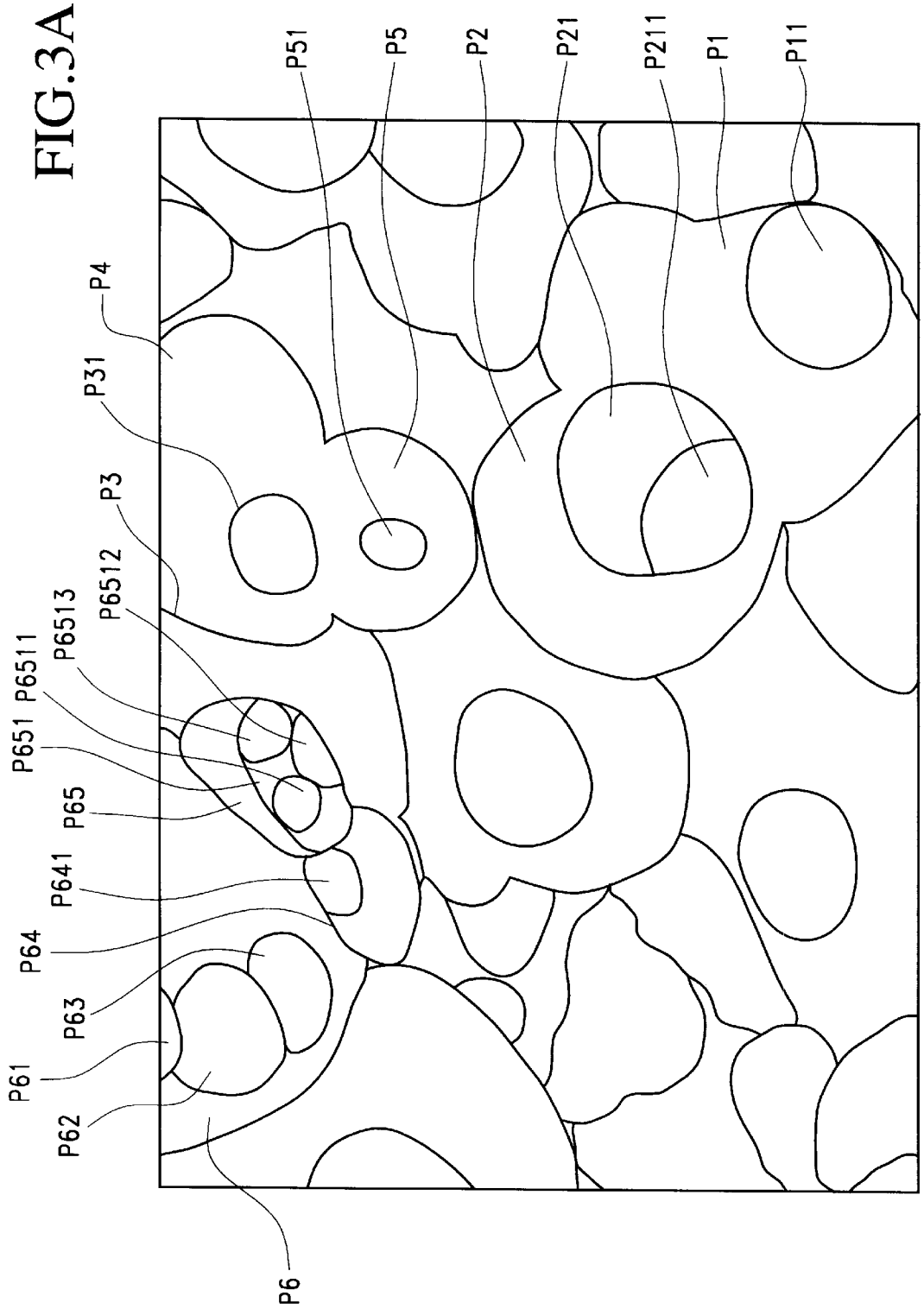

ORTHOPEDIC IMPLANT HAVING A POROUS SURFACE AND METHOD OF MAKING SAME

FIELD OF THE INVENTION

The present invention relates to an orthopedic implant having a porous surface and a method for making such an orthopedic implant.

BACKGROUND OF THE INVENTION

The porous surface of the orthopedic implant is generally provided with a plurality of pores ranging in diameter between 10 and 500 microns. The bone tissues are thus capable of growing in the pores so as to unite the implant with the bone tissues. The conventional methods for making the implant with a porous surface include the plasma spray process, the sintering process, and the diffusion bonding process. The pores formed by the plasma spray process are not in communication with the outside, as shown in "A", "B", pores of FIG. 1. As a result, the bone tissues can not grow into them. On the other hand, they tend to form boundaries which are susceptible to breakage. The boundaries refer to the interfaces between the pores and the bone tissues. Similarly, the pores formed by the sintering process are not in communication with the outside and are susceptible to poor fatigue strength. As a result, the plasma spray process and the sintering process (either sintered beads or sintered fiber metal) can not be used to make the main structure of the orthopedic implant (Richard J. Friedman, et al., entitled "Current Concepts in Orthopaedic Biomaterials and Implant Fixation", The Journal of Bone and Joint Surgery, Vol. 75-A, No. 7, July 1993). The diffusion bonding process, such as vapor deposition techniques for making the porous tantalum structure, can be used to make pores free from the drawbacks as described above [J. Dennis Bobyn, Michael Tanzer, and Jo E. Miller: Fundamental Principles of Biologic Fixation. In Morrey BF (ed): Reconstructive Surgery of The Joints. Churchill Livingstone, 1996, pp 75–94]. However, such porous structure has a relatively poor bending strength and is therefore vulnerable to deformation or damage by a bending force exerting thereon. Moreover, the porous titanium structure is not cost-effective.

SUMMARY OF THE INVENTION

It is the primary objective of the present invention to provide an orthopedic implant having a porous surface.

It is another objective of the present invention to provide an orthopedic implant having a pores-within-a-pore porous surface structure.

It is still another objective of the present invention to provide an orthopedic implant having a pores-within-a-pore porous surface structure, with a pore opening ranging in size between 10 and 800 microns.

It is still another objective of the present invention to provide a method for making an orthopedic implant having a porous surface.

The present invention provides an electrochemical technique employing a large electric current density and/or an intermediate electric current density for forming a pores-within-a-pore porous structure on a metal surface such that the porous structure is in communication with the outside, and that the porous structure is circumvented by a metal substrate. As a result, the porous structure is not vulnerable to boundary severance, poor fatigue strength and/or-bending.

BRIEF DESCRIPTION OF THE DRAWINGS

FIG. 3A is another SEM picture of the orthopedic implant made in Example 1 of the present invention.

FIGS. 6A to 15A are SEM pictures of the orthopedic implants made by Examples 3 to 12 of the present invention, respectively.

FIGS. 6B to 15B are optical microscopic pictures of the orthopedic implants made by Examples 3 to 12 of the present invention, respectively.

DETAILED DESCRIPTION OF THE INVENTION

Figure 1:
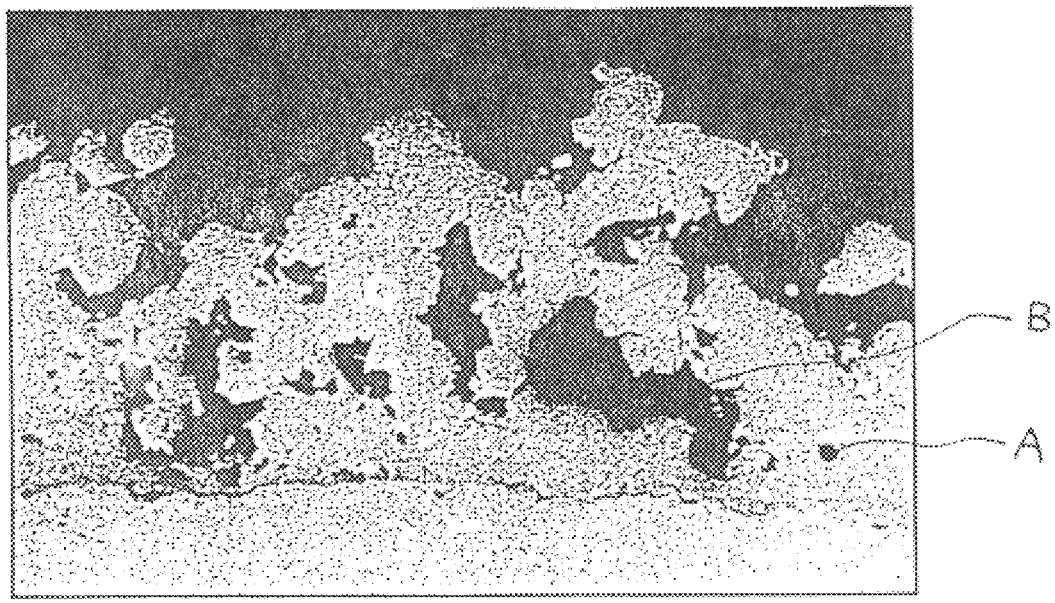
FIG. 1 shows an optical microscopic picture of a hip stem made by he conventional plasma spray process.

The orthopedic implant of the present invention has a porous surface with a plurality of pores, some of which are pores-within-a-pore porous structures. At least some of the pores-within-a-pore porous structures have an opening ranging in diameter between 10 and 800 microns, preferably between 50 and 600 microns, and more preferably between 100 and 500 microns.

The examples of the orthopedic implants are hip stem, screws, fixation rods, hooks, cages, etc. The orthopedic implants are made of any conventional biologically compatible material, such as the unitary metal, alloy, or metal or nonmetal coated with a metal layer (unitary metal layer or alloy layer) or with multiple metal layers.

The above orthopedic implants according to the present invention have at least the pores-within-a-pore porous structure for bone ingrowth, as well as the conventional non-pores-within-a-pore porous structure on their surface.

The pores-within-a-pore porous structures of the present invention have pores (the first-stepped pores), within some of which there are pores (the second-stepped pores), within some of the second-stepped pores there are pores (the third-stepped pores), and so on even up to sixth-stepped pores. The pores-within-a-pore porous structures of the present invention may comprise any combinations of differently stepped pores, such as the first-stepped pores; the first-stepped pores within which there are only the second-stepped pores; the first-stepped pores within which there are the second-stepped pores and the third-stepped pores; the first-stepped pores within which there are the second-stepped pores, the third-stepped pores and the fourth-stepped pores, and so on. Within the same first-stepped pore may have one or more second-stepped pores, and within the same second-stepped pore may have one or more third-stepped pores, and so on.

The above pores may have any shape, which may be a regular geometric form, such as circular, cylindrical, and oval; or irregular.

The pore opening used herein, unless indicated otherwise, refers to the opening of the first-stepped pore facing outward (away from the substrate). If the stepped pore has an opening which is round or circle-like, the size of the opening refers to the circle diameter. If it is irregular in shape, the size of the opening refers to the average of the maximum distance and the minimum distance of the opening. Similarly, the opening of the two-stepped pore is referred to as the two-stepped opening. The opening of the three-stepped pore is referred to as the three-stepped opening, etc.

The high-stepped (two-stepped, three-stepped, four-stepped . . . ) openings of the pores-within-a-pore porous structure of the present invention have the size ranging between 10 and 500 microns, preferably between 50 and 400 microns, and most preferably between 50 and 300 microns.

The number of the pores-within-a-pore porous structures have a pore opening ranging in diameter between 10 and 800 microns is preferably over 30% of the total number of said pores-within-a-pore porous structures, more preferably over 50%, and most preferably over 80%.

The high-stepped pores having a pore opening ranging between 10 and 500 microns are preferably over 20% of the total number of the high-stepped pores of the pores-within-a-pore porous structures, more preferably over 40%, and most preferably over 70%.

The number of the first-stepped pores within which there is no high-stepped pores is less than 70% of the total number of said plurality of pores, preferably less than 50%, and more preferably less than 40%.

The above pores, either the first-stepped pores or the high-stepped pores, may be superimposed. For example, a plurality of first-stepped pores are partially superimposed such that the superimposing portions form the second-stepped pores, and within the first-stepped pore two or more second-stepped pores are superimposed, and thus forming three-stepped pores in the superimposing portion.

Any conventional methods may be used to control on which parts of the surface the pores-within-a-pore porous structure. For example, a etching-resistant layer may be coated or a Teflon® sealing tape may be put on the surface on which no pores-within-a-pore porous structure is to be formed during the formation of the pores-within-a-pore porous structure.

The process for making the orthopedic implant having a porous surface according to the present invention comprise:

forming a plurality of initial pores on at least one portion of a surface of an orthopedic implant having; and forming a pores-within-a-pore structure within the plurality of initial pores, wherein an intermediate electric current density pore etching method is used to form said pores-within-a-pore structure.

The definitions of the above orthopedic implant, the pores-within-a-pore porous structure, the pore opening and the size of the pore opening are the same as described above.

A suitable method for forming said plurality of initial pores on at least one portion of the surface of the orthopedic implant may be the conventional methods, such as the laser drilling, the high pressure water drilling, chemical pore etching, and the electrochemical pore etching method described below. The initial pores are substantially first-stepped pores having an opening ranging between 0.2 and 500 microns, preferably between 0.5 and 200 microns, most preferably between 1 and 100 microns. The initial pores may contain one or more high-stepped pores formed by the method of the present invention.

Preferably, the method for forming said plurality of initial pores on at least one portion of the surface of the orthopedic implant makes use of the electrochemical pore etching method, and more preferably the high electric current density pore etching method, in which the orthopedic implant is submerged in an electrolyte solution to carry out the electrolysis by an electric current density higher than 0.2 A/cm$^2$. The electrolysis is carried out by the conventional methods in existence, such as the three-electrode potentiostat electrolysis, two-electrode potential control electrolysis, the pulse electrolysis, and the galvanostat electrolysis, etc.

The above electrolyte solution may be a solution containing supporting electrolyte, or preferably a solution containing an electrolyte capable of etching pores, such as HCl, NaCl, NaF, HF, etc., preferably NaCl. The electrolyte solution containing 1–8% by weight of NaCl, or preferably 2–5% by weight of NaCl, is recommended.

As far as the high electric current density pore etching method is concerned, the electrolysis conditions are adjustable depending on the nature of the orthopedic implant, provided that the electric current density is greater than 0.2 A/cm$^2$, more preferably 0.3 A/cm$^2$, and most preferably 0.5 A/cm$^2$. The electrolysis conditions include (but not limited to) electrolyte concentration, electrolysis temperature, electrolysis time, electrolysis potential (the potential between the reference electrode and the working electrode in the three-electrode potentiostat electrolysis; and the applied potential between the anode and cathode).

Generally speaking, the conductivity of the electrolyte solution is preferably greater than 10 S, and more preferably not less than 20 S, so as to attain the electric current density greater than 0.2 A/cm$^2$. The correlation between the conductivity and the electrolyte concentration of the electrolyte solution can be found in the Chemistry or Chemical Engineering Handbooks.

In order to facilitate the high electric current density electrolysis, an elevated electrolysis temperature is preferable, but is not to exceed 80° C. to avoid undesired vigorous reaction. A suitable elect rolysis temperature will be ambient temperature to 60° C., and preferably to 50° C.

The time of the high electric current density electrolysis ranges between 30 seconds and 5 minutes, preferably between 1 and 4 minutes, most preferably between 1 and 3 minutes, for formation of the initial pores with the size of opening thereof being in the range of 0.2–500 microns.

Said intermediate electric current density pore etching method used in the process of the present invention is similar to the high electric current density pore etching method, except that the electric current density ranges between 0.05 A/cm$^2$ and 1 A/cm$^2$, preferably between 0.1 A/cm$^2$ and 0.8 A/cm$^2$, most preferably between 0.2 A/cm$^2$ and 0.7 A/cm$^2$; and the electrolysis time preferably ranges between 3 and 30 minutes, and more preferably between 5 and 20 minutes.

The intermediate electric current density pore etching method may be same or different from the high electric current density pore etching method in electrolyte solution, and electrolysis temperature, but preferably same in electrolyte solution, and electrolysis temperature.

EXAMPLE 1

Figure 2:
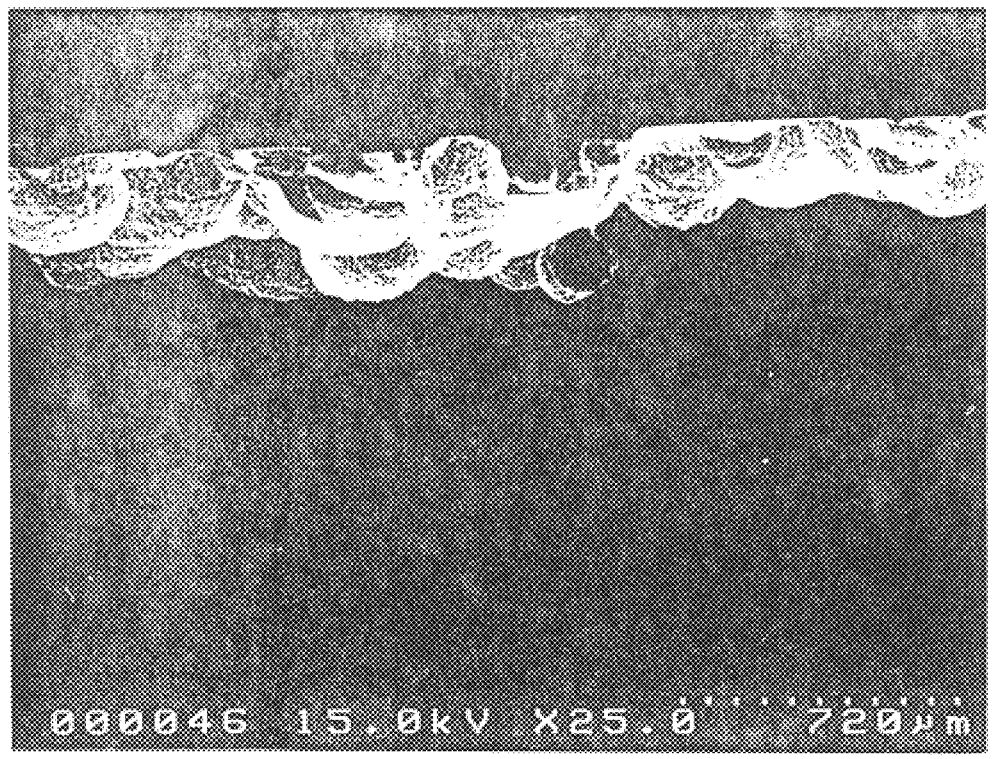
FIG. 2 is a scanning electron microscopic (SEM) picture of an orthopedic implant made in Example 1 of the present invention.
Figure 3B:
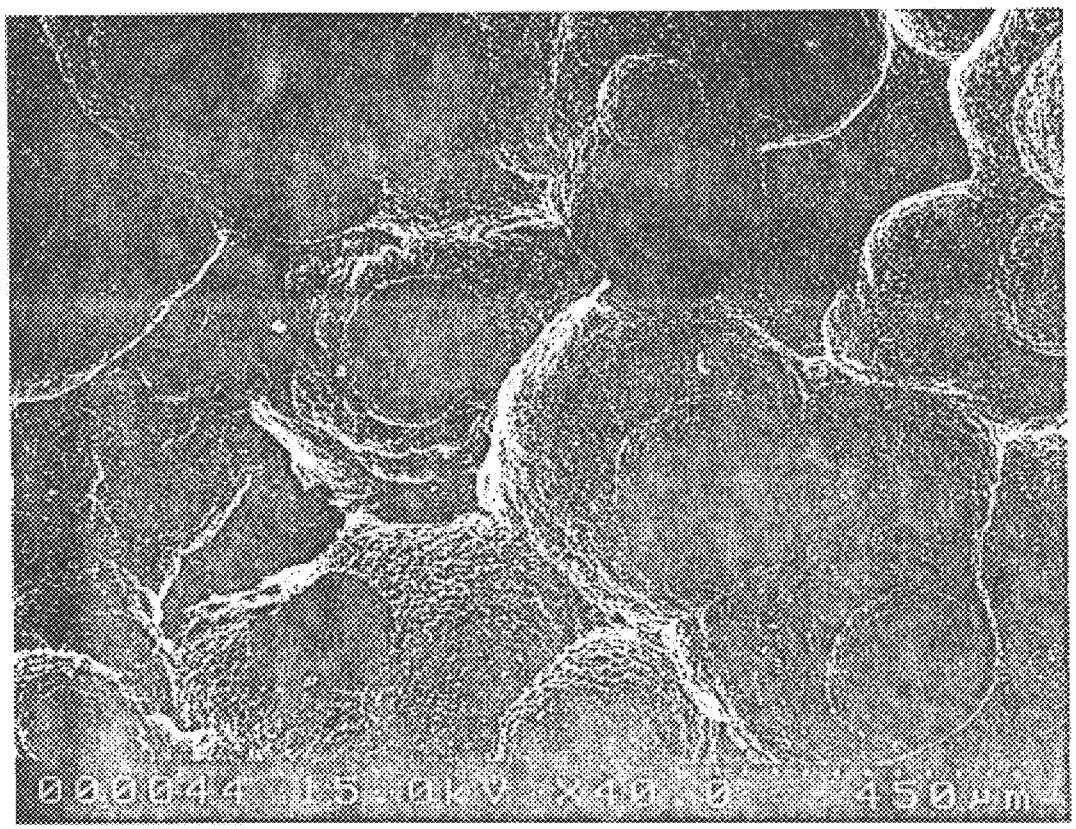
FIG. 3B is a plot of FIG. 3A labeling pores of the pores-within-a-pore structure.

A rectangular cage having a surface area of about 3.5 cm$^2$ was electrolyzed for 2 minutes in 3.5 wt % NaCl electrolyte solution at room temperature by a constant current of 2.0 A/cm$^2$. Thereafter, a constant electric current of 1.0 A/cm$^2$ was used to carry out the electrolysis for 5 minutes. The results are shown in the scanning electron microscopic (SEM) pictures of FIGS. 2 and 3A. As shown in FIG. 2, the cage is provided with the pores-within-a-pore porous structure. Referring to FIGS. 3A and 3B, P1, P2, P3, P4, P5, and P6 are all first-stepped pores with the pore openings being respectively about 450 μm, about 500 μm, about 320 μm, about 350 μm, 800 μm. P11, P21, and P51 are second-stepped pores within the first-stepped pores P1, P2, and P5, respectively, and the pore opening of the second-stepped pores P11, P21, and P51 are about 225 μm, about 270 μm, and about 150 μm, respectively. P31 is a common second-stepped pore of the first-stepped pores P3, P4 and P5. The pore opening of the common second-stepped pore P31 is about 150 μm. P61, P62, P63, P64 and P65 are the second-stepped pores of a first-stepped pore P61, and their opening respectively are about 225 μm, about 225 μm, about 180 μm, about 225 μm, and about 270 μm. P651 is a third-stepped pore of the second-stepped pore P65, whose opening size is about 200 μm. P6511, P6512, and P6513 are fourth-stepped pores of the third-stepped pore P651, with the sizes of openings thereof being about 100 μm, about 100 μm, and about 90 μm.

EXAMPLE 2

This example uses the two-stage electrolysis procedures similar to that of the Example 1. The current density (the electrolysis time) for forming a pores-within-a-pore structure on a surface of a fixation rod in the two electrolysis stages were respectively 0.65 A/cm$^2$ (30 seconds) and 0.2 A/cm$^2$ (6 minutes).

Figure 4:
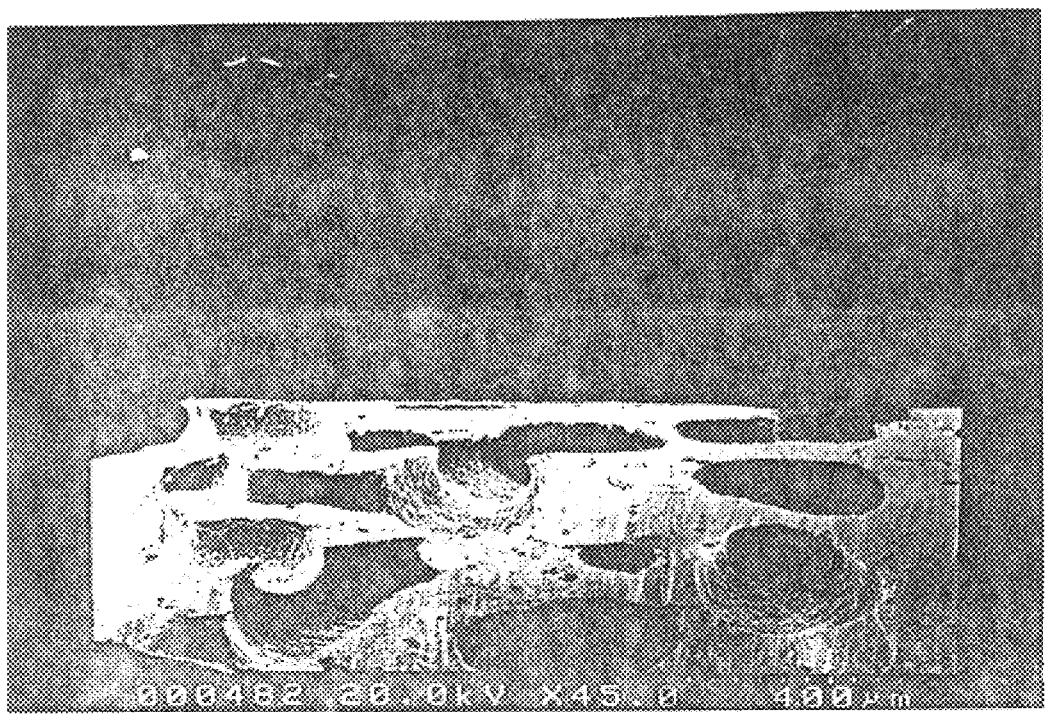
FIG. 4 is a SEM picture of an orthopedic implant made in Example 2 of the present invention.
Figure 5:
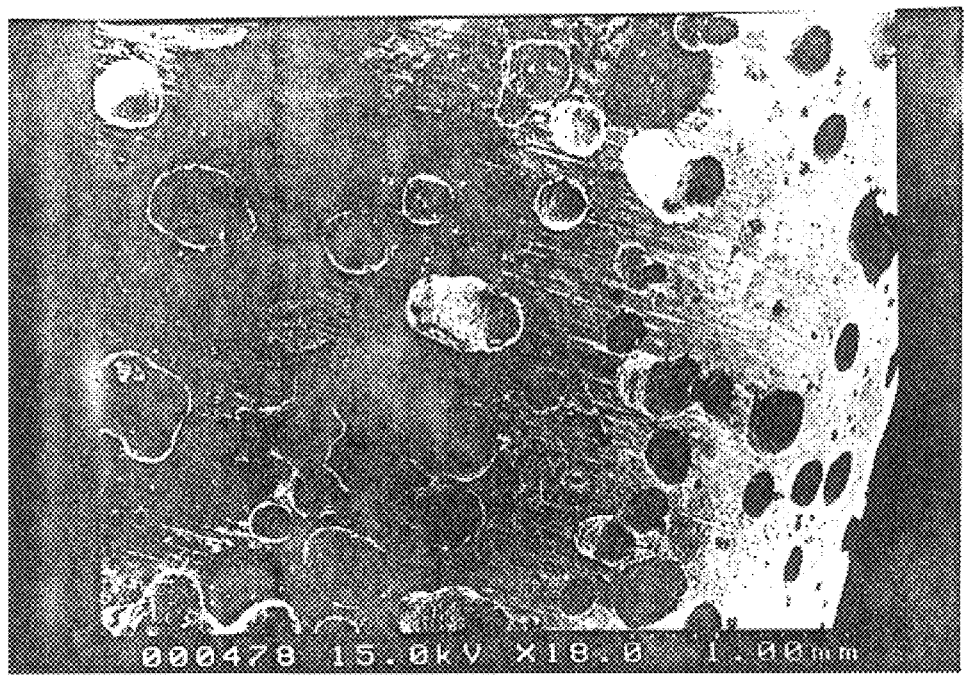
FIG. 5 is another SEM picture of the orthopedic implant made in Example 2 of the present invention.
Figure 6A:
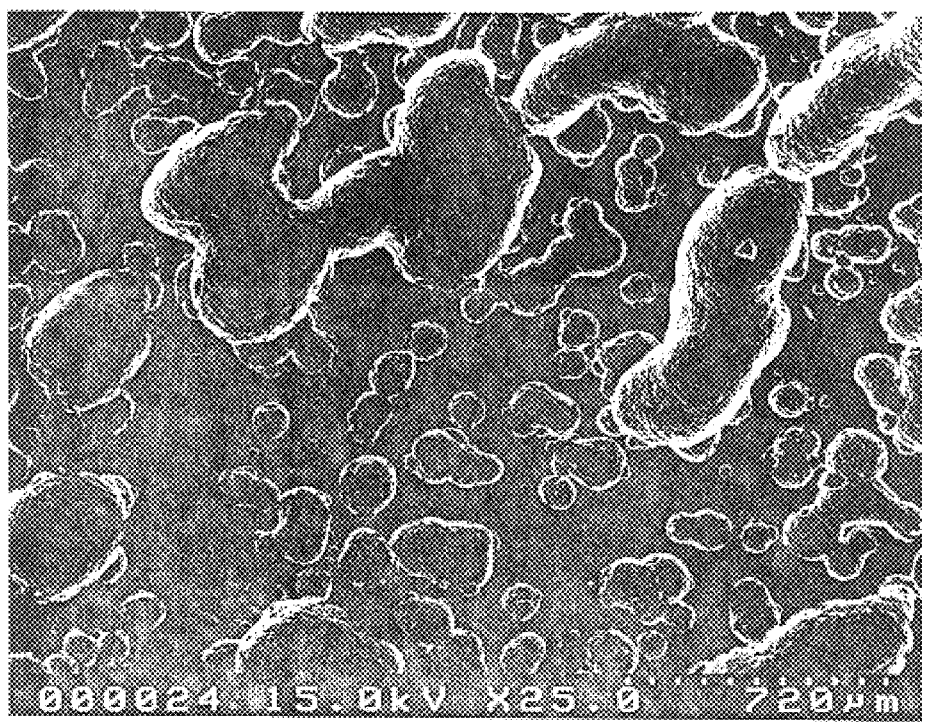
Figure 6B:
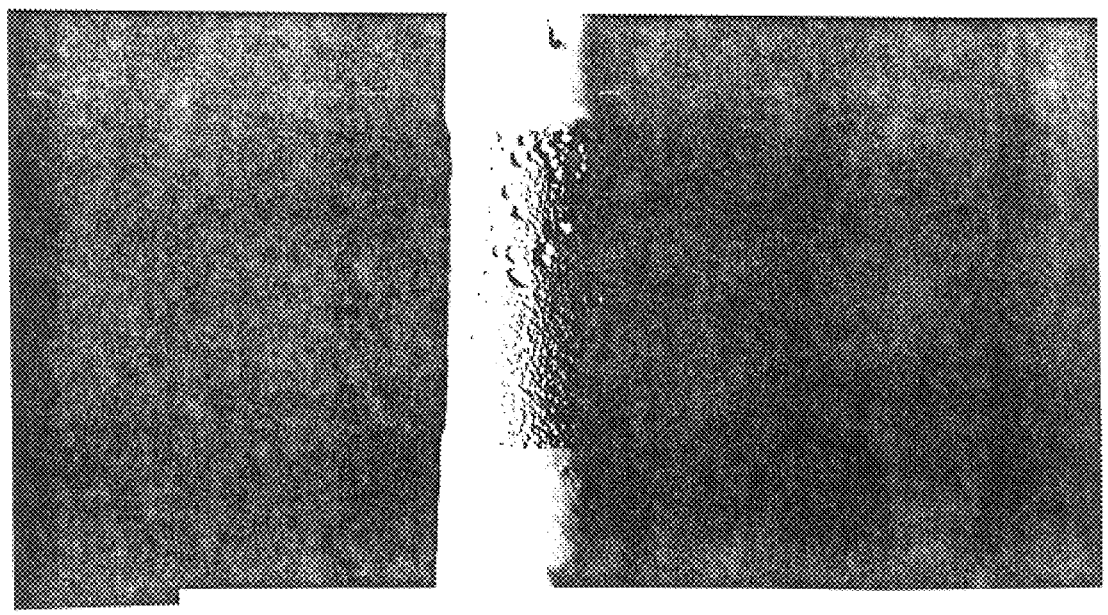
Figure 7A:
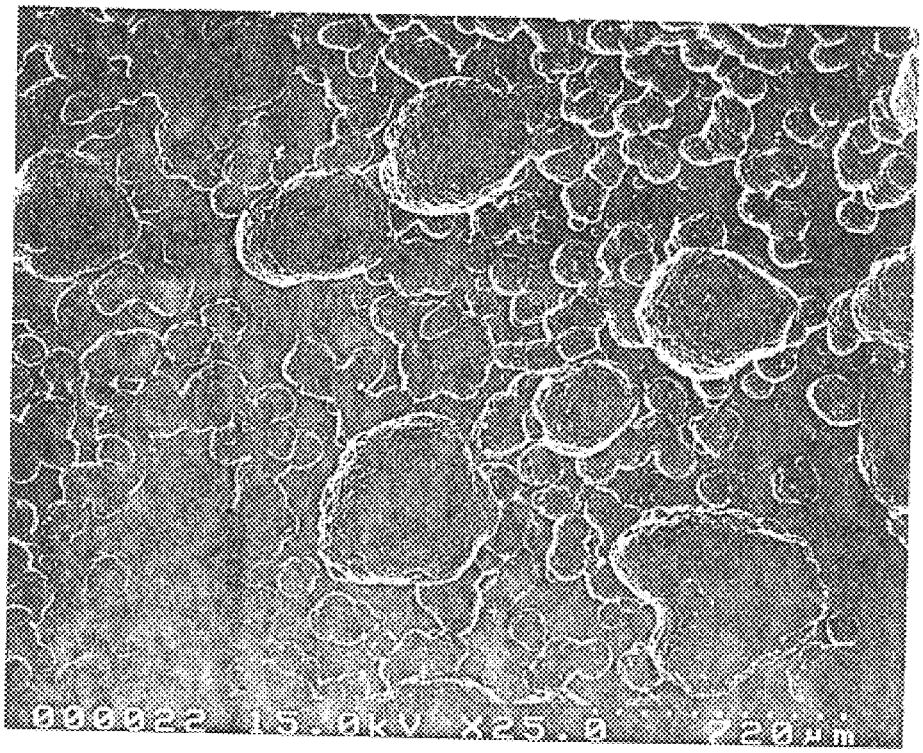
Figure 7B:
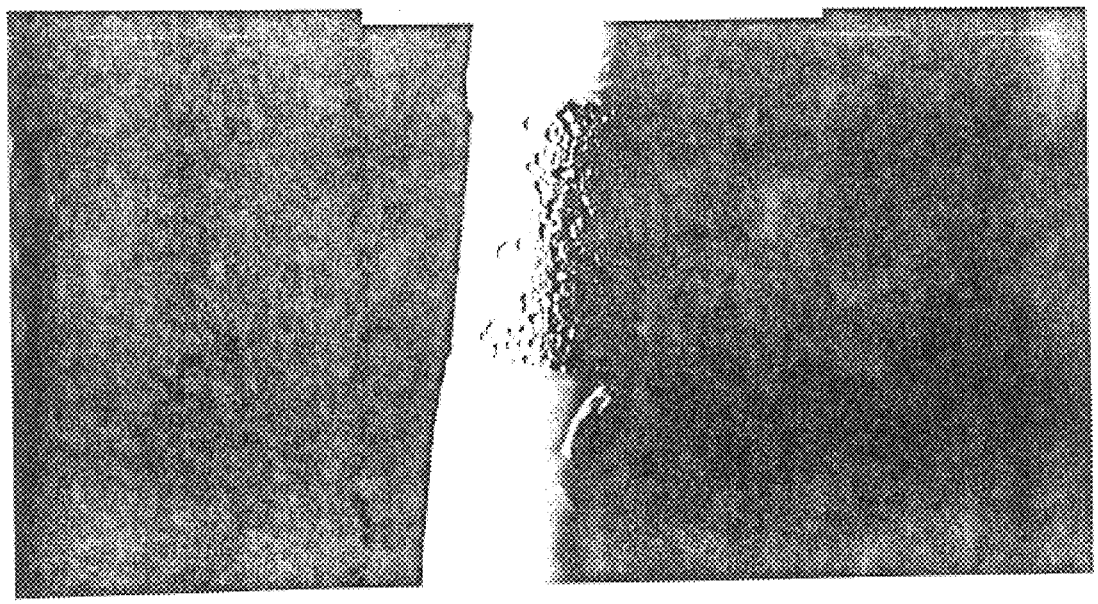
Figure 8A:
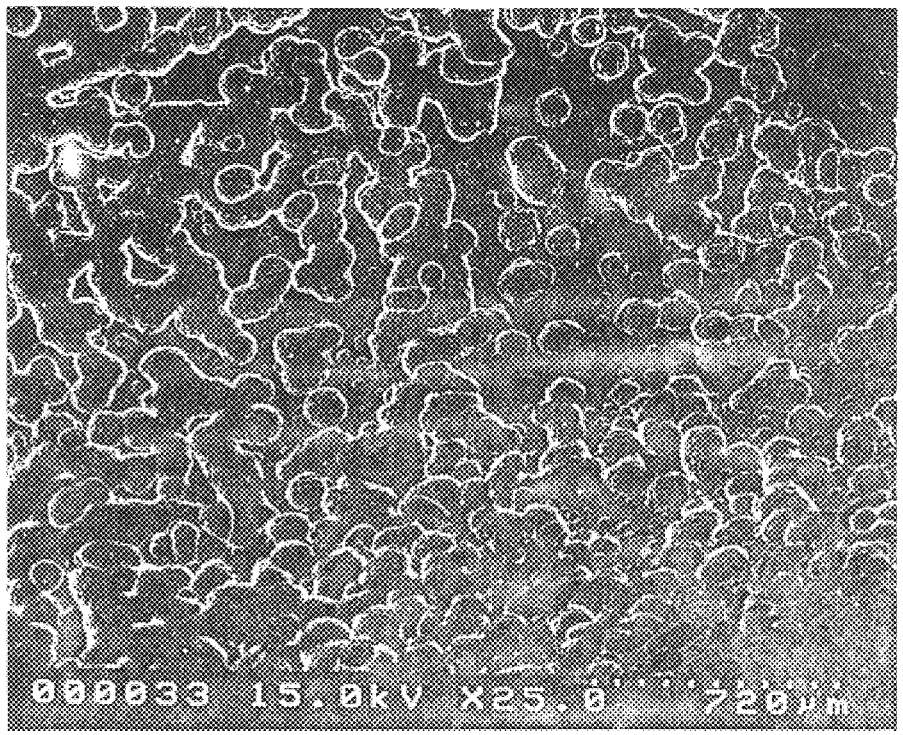
Figure 8B:
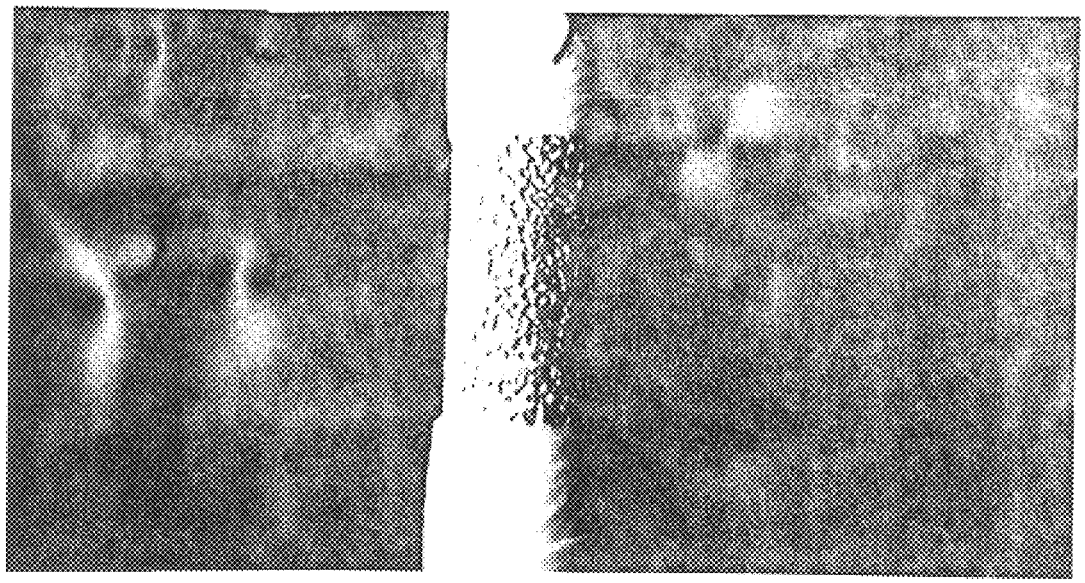
Figure 9A:
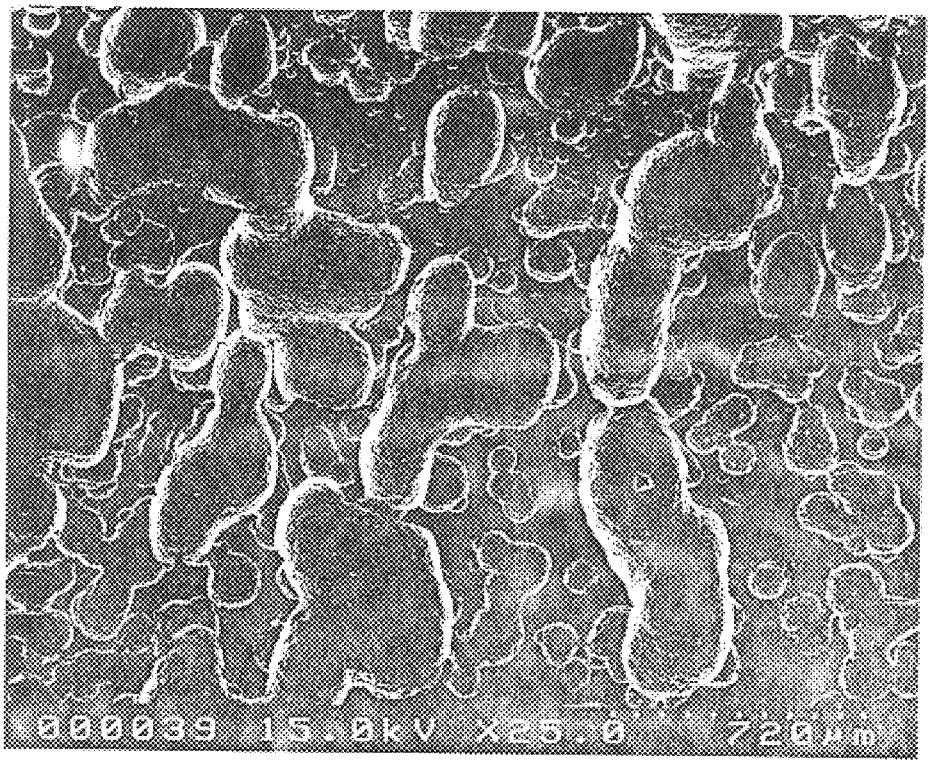
Figure 9B:
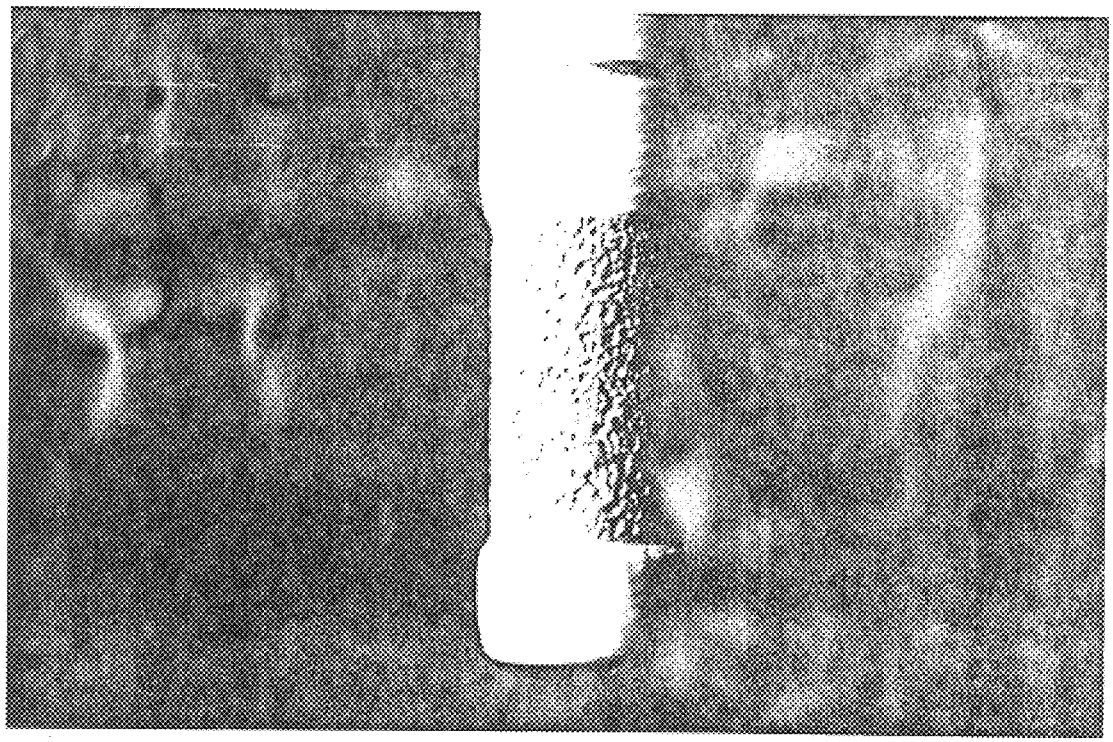
Figure 10A:
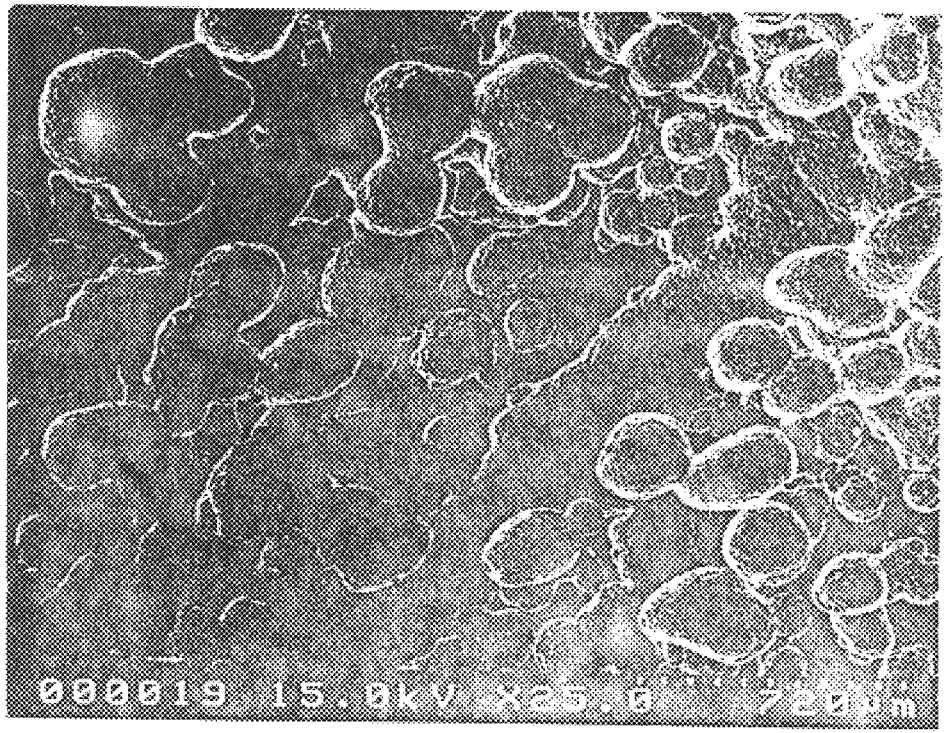
Figure 10B:
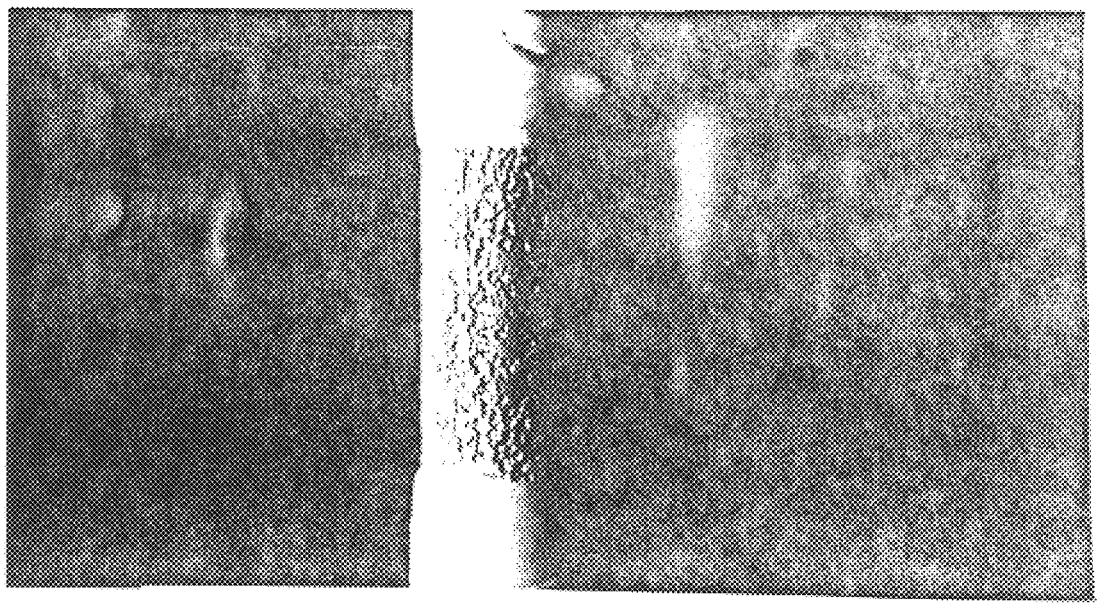
Figure 11A:
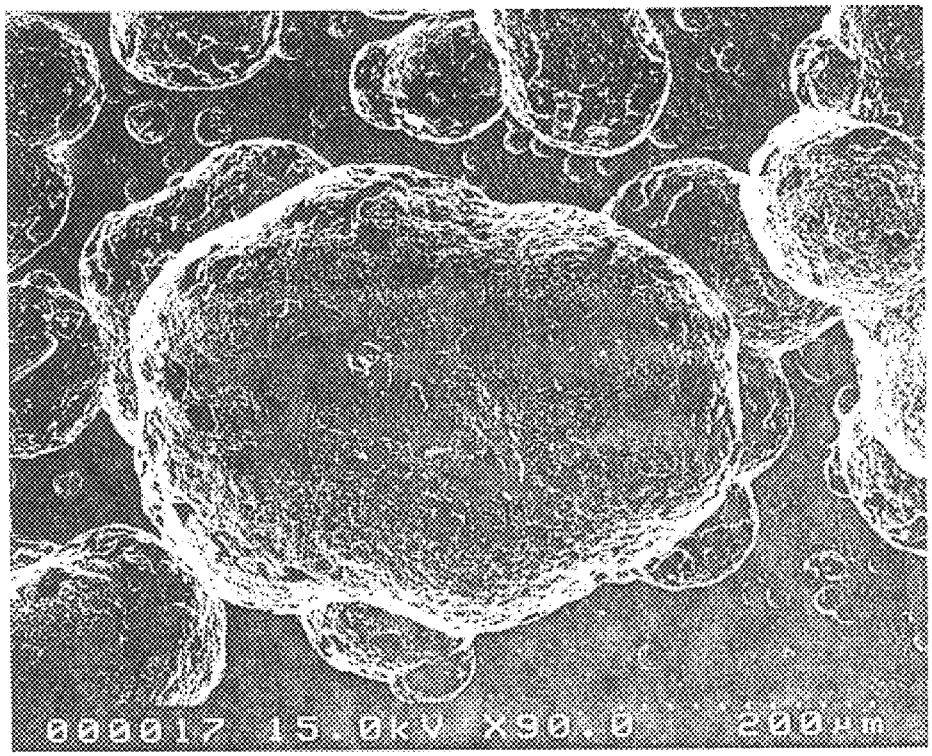
Figure 11B:
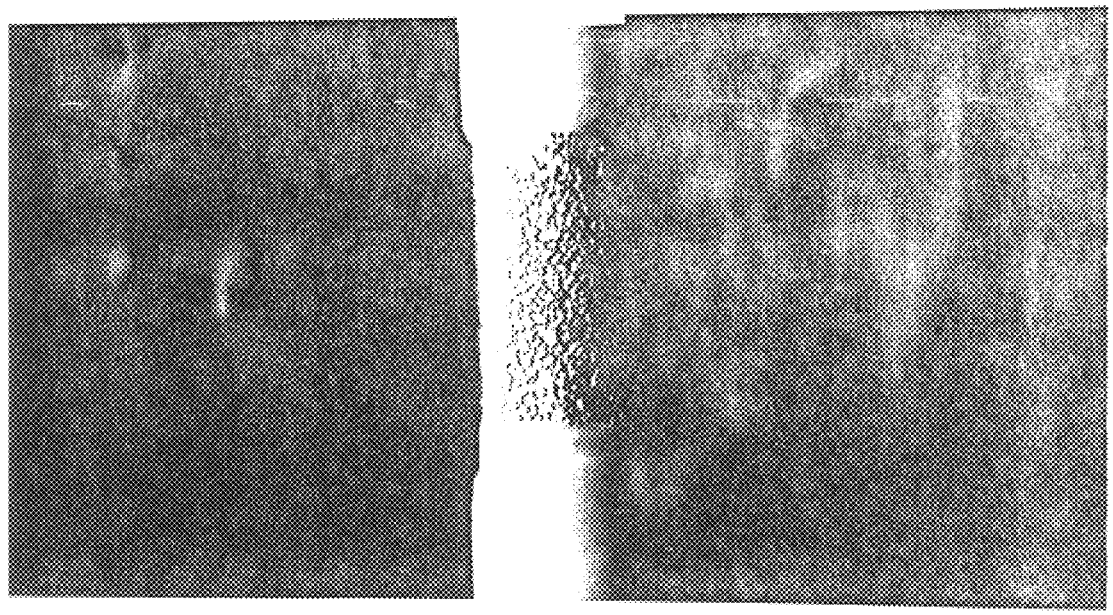
Figure 12A:
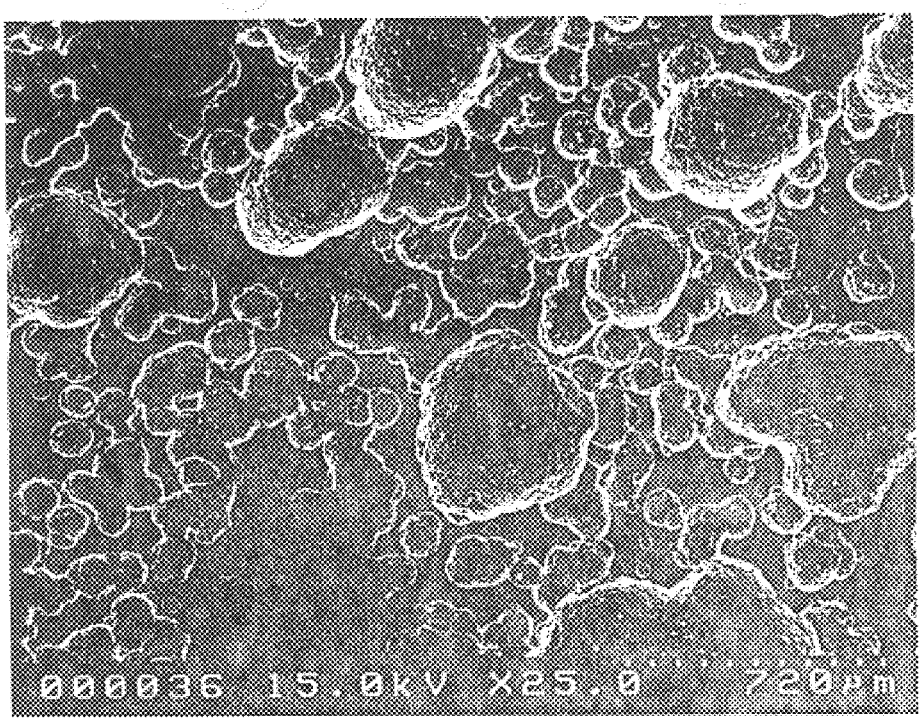
Figure 12B:
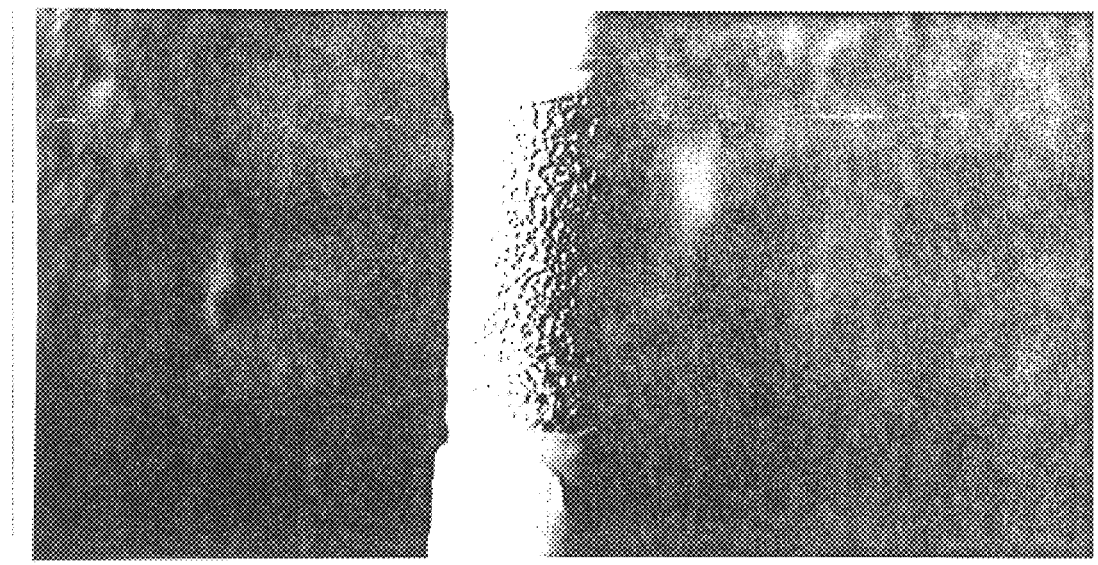
Figure 13A:
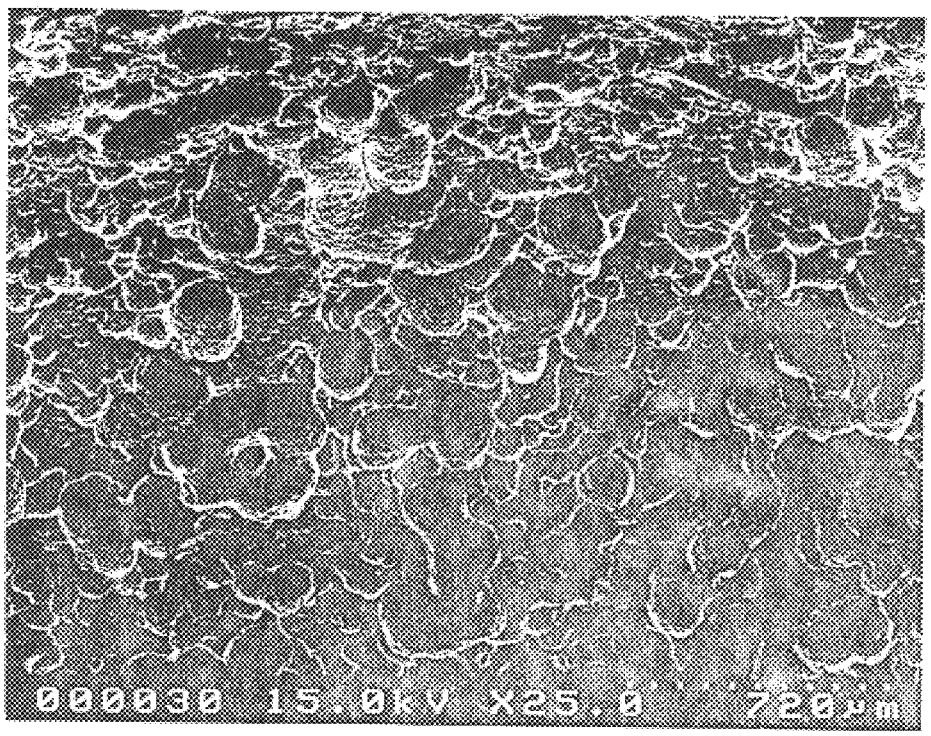
Figure 13B:
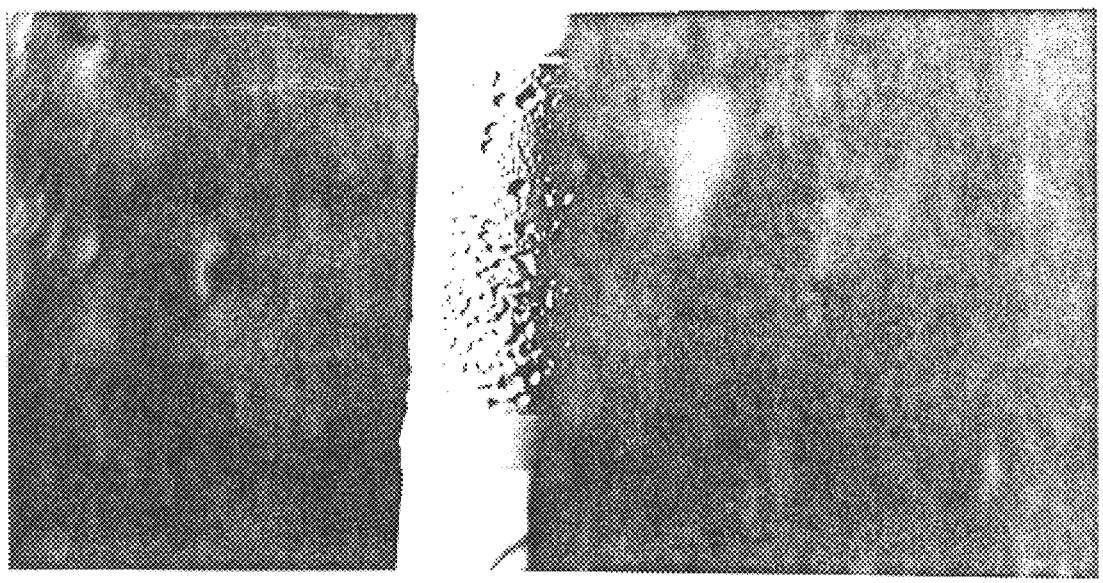
Figure 14A:
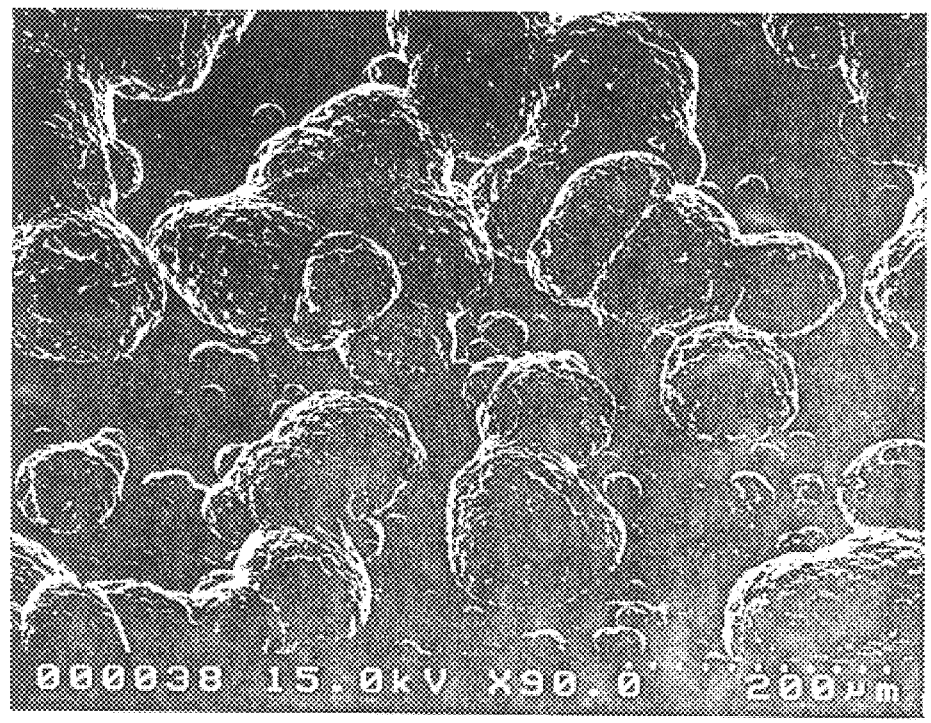
Figure 14B:
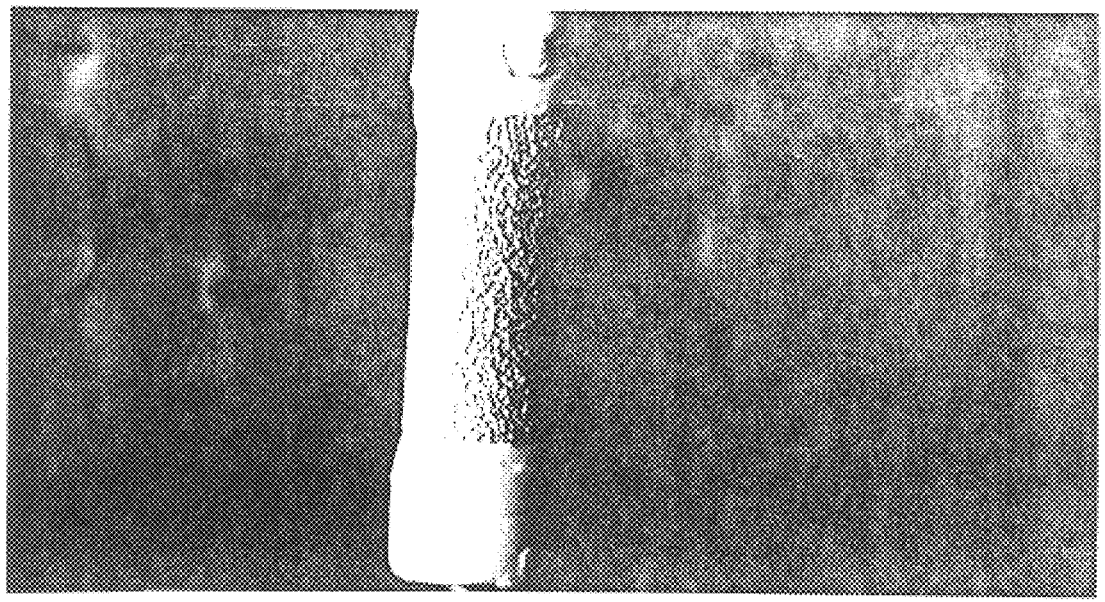
Figure 15A:
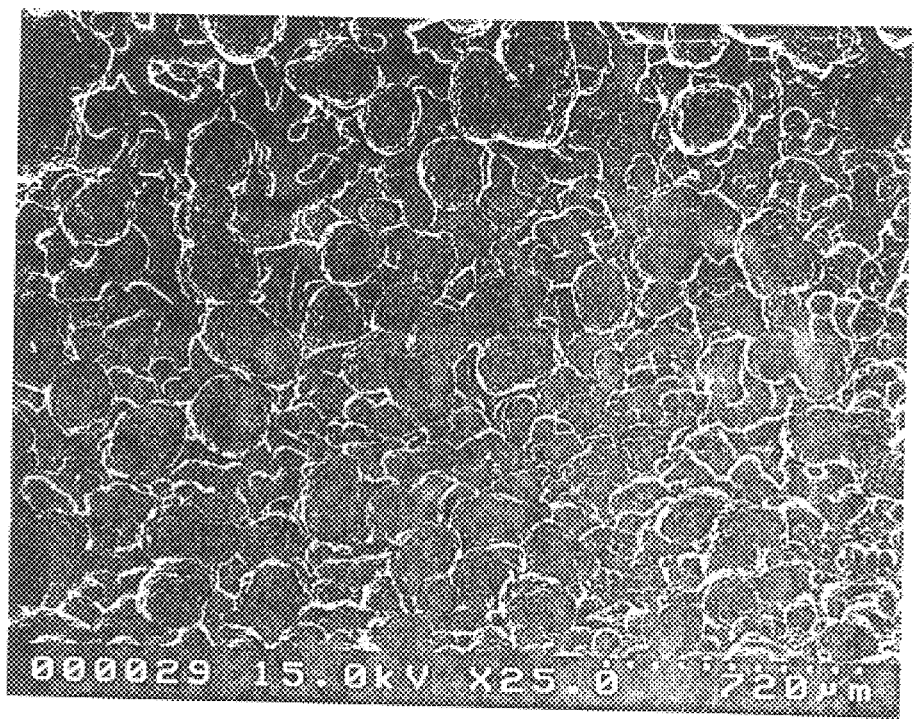
Figure 15B:
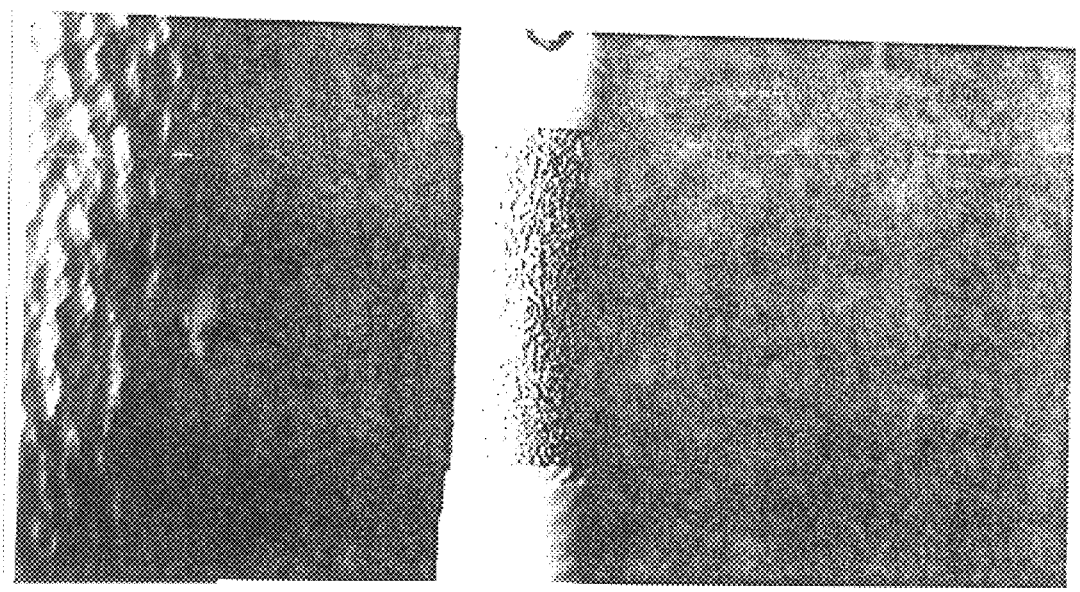

The results are shown in FIGS. 4 and 5. FIG. 4 is a scanning electron microscope (SEM) picture taken in the direction perpendicular to the central axis of the fixation rod, in which the surface of the fixation rod is provided with the pores-within-a-pore porous structure. FIG. 5 is a SEM picture of the surface of the fixation rod showing that the distribution and the size of the pores are uniform, and that the overlapping of the first-stepped pores is not serious.

EXAMPLES 3–12

A fixation rod was electrolyzed for one minute with a constant current of 2.0 A in 3.5 wt % NaCl electrolyte solution at room temperature. Thereafter, the fixation rod was electrolyzed with a constant current density electrolysis in accordance with the conditions listed in Table 1. The fixation rod has a surface area of 3.14 cm$^2$. The results of Examples 3–12 are shown in Table 1.

The results are also shown in FIGS. 6A–15A, and FIGS. 6B–15B. FIGS. 6A–15A show SEM pictures of the surfaces of the fixation rods. FIGS. 6B–15B show the optical microscopic pictures of the surfaces of the fixation rods.

TABLE 1

| Ex. | Electric current (A) | Electric current density (A/cm$^2$) | Electrolysis time (min) | Pore distribution uniformity | Pore distribution density | Pore depth | n-stepped Pore | SEM picture |
| --- | --- | --- | --- | --- | --- | --- | --- | --- |
| 3 | 0.2 | 0.064 | 5.0 | X | X | X | 1–2 | 6A |
| 4 | 0.3 | 0.095 | 8.3 | Δ | Δ | Δ | 1–3 | 7A |
| 5 | 0.4 | 0.127 | 6.25 | 0 | Δ | Δ | 2–3 | 8A |
| 6 | 0.5 | 0.159 | 5.0 | Δ | Δ | 0 | 2–3 | 9A |
| 7 | 0.5 | 0.159 | 6.0 | 0 | 0 | 0 | 2–4 | 10A |
| 8 | 0.5 | 0.159 | 8.0 | 0 | 0 | 0 | 2–4 | 11A |
| 9 | 0.5 | 0.159 | 10.0 | 0 | 0 | 0 | 2–4 | 12A |
| 10 | 0.5 | 0.159 | 15.0 | 0 | 0 | 0 | 2–4 | 13A |
| 11 | 1.0 | 0.318 | 2.5 | ⊙ | ⊙ | ⊙ | 2–4 | 14A |
| 12 | 2.0 | 0.637 | 1.25 | 0 | 0 | 0 | 2–3 | 15A |

X: poor; Δ: fair; 0: good; ⊙: excellent

In the above examples, the SEM pictures were taken by the product S-4100 made by Hitachi Corp. of Japan. The operation conditions were: 23° C., 10−9 torr. The acceleration voltage and the amplification rates are all labeled on the SEM pictures.

In electrolysis, the working electrode was anode and made of titanium. The counter electrode was cathode and made of 316 stainless steel. The surface area of the counter electrode is greater than the electrolysis area of the working electrode.

What is claimed is:

1. An orthopedic metal implant comprising at least one outer surface having a plurality of pores on at least a portion of said outer surface, wherein part of the plurality of pores have a pores-within-a-pore porous structure, said pores-within-a-pore porous structure comprising a first pore on the outer surface of the implant and at least one second pore within the first pore and wherein said first pore has a pore opening ranging in size between 10 and 800 microns.

2. The orthopedic implant as defined in claim 1 which second pores within the first pore contain sequentially n additional pores within each pore wherein n is 3, 4, 5 or 6.

3. The orthopedic implant as defined in claim 1, wherein at least 30% of said plurality of pores have said pores-within-a-pore porous structure, and said second-stepped pore has a pore opening ranging in size between 10 and 500 microns.

4. The orthopedic implant as defined in claim 2, wherein at least 50% of said plurality of pores have said pores-within-a-pore porous structure, said first-stepped pore has a pore opening ranging in size between 50 and 600 microns, and said second-stepped pore has a pre opening ranging in size between 50 and 400 microns.

5. The orthopedic implant as defined in claim 2, wherein said first-stepped pore an opening ranging in size between 100 and 500 microns, and said second-stepped pore has a pore opening ranging in size between 50 and 300 microns.

6. The orthopedic implant as defined in claim 1 which is selected from the group consisting of a hip stem, screw, fixation rod, hook and cage.

7. The orthopedic implant as defined in claim 2 which is selected from the group consisting of a hip stem, screw, fixation rod, hook and cage.

8. The orthopedic implant as defined in claim 3 which is a hip stem, screw, fixation rod, hook and cage.

9. The orthopedic implant as defined in claim 4 which is selected from the group consisting a hip stem, screw, fixation rod, hook and cage.

10. The orthopedic implant as defined in claim 5 which is selected from the group consisting a hip stem, screw, fixation rod, hook and cage.

* * * * *